(12) United States Patent
Cooker et al.

(10) Patent No.: US 7,399,726 B2
(45) Date of Patent: Jul. 15, 2008

(54) PROCESS FOR DIRECT OXIDATION OF PROPYLENE TO PROPYLENE OXIDE AND LARGE PARTICLE SIZE TITANIUM SILICALITE CATALYSTS FOR USE THEREIN

(75) Inventors: Bernard Cooker, Malvern, PA (US); Wilson H. Onimus, Holmes, PA (US); Jennifer D. Jewson, Boyertown, PA (US); Ralph M. Dessau, Edison, NJ (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 397 days.

(21) Appl. No.: 11/087,776

(22) Filed: Mar. 23, 2005

(65) Prior Publication Data

US 2005/0187395 A1 Aug. 25, 2005

Related U.S. Application Data

(62) Division of application No. 10/251,405, filed on Sep. 20, 2002, now Pat. No. 6,960,671.

(51) Int. Cl.
*B01J 29/06* (2006.01)
*B01J 29/89* (2006.01)
*B01J 29/068* (2006.01)

(52) U.S. Cl. .............................. 502/64; 502/66; 502/74; 423/713

(58) Field of Classification Search ................ 423/713; 549/531, 532, 533; 502/64, 66, 74
See application file for complete search history.

(56) References Cited

U.S. PATENT DOCUMENTS

| | | | |
|---|---|---|---|
| 3,351,635 A | 11/1967 | Kollar | |
| 4,367,342 A | 1/1983 | Wulff et al. | |
| 4,410,501 A | 10/1983 | Taramasso et al. | |
| 4,833,260 A | 5/1989 | Neri et al. | |
| 5,263,090 A | 11/1993 | Hughes | |
| 5,354,875 A | 10/1994 | Nemeth et al. | |
| 5,401,486 A | 3/1995 | Mueller et al. | |
| 5,500,199 A | 3/1996 | Bellussi et al. | |
| 5,859,265 A | 1/1999 | Müller et al. | |
| 5,972,661 A | 10/1999 | Kubera et al. | |
| 6,005,123 A | 12/1999 | Dessau et al. | |
| 6,008,389 A * | 12/1999 | Grosch et al. ............... | 549/533 |
| 6,106,803 A | 8/2000 | Hasenzahl et al. | |

FOREIGN PATENT DOCUMENTS

| | | |
|---|---|---|
| BE | 1 011 375 A6 | 10/1997 |
| DE | 196 00 709 A1 | 7/1997 |
| EP | 0 100 118 | 7/1983 |
| EP | 0 543 247 A1 | 11/1992 |
| EP | 0 638 362 A1 | 2/1995 |
| EP | 0 893 158 A1 | 6/1998 |
| WO | WO 97/47386 | 12/1997 |
| WO | WO 98/00413 | 1/1998 |
| WO | WO 01/72420 A1 | 10/2001 |

OTHER PUBLICATIONS

J.F. Bengoa et al., "Influence of TS-1 Structural Properties and Operation Conditions on Benzene Catalytic Oxidation with $H_2O_2$," Microporous and Mesoporous Materials 24 (1998) 163-172.
C. Perego et al., "Production of Titanium Containing Molecular Sieves and Their Application in Catalysis," Applied Catalysis A: General 221 (2001) 63-72.
W. Laufer et al., "Direct Oxidation of Propylene and Other Olefins on Precious Metal Containing Ti-Catalysts," Applied Catalysis A: General 213 (2001) 163-171.
Gang Li et al., "Epoxidation of Propylene Using Supported Titanium Silicalite Catalysts," Applied Catalysis A: General 236 (2002) 1-7.
M.G. Clerici et al., "Epoxidation of Lower Olefins with Hydrogen Peroxide and Titanium Silicalite," Journal of Catalysis 140, 71-83 (1993).
J.R. Monnier, "The Direct Epoxidation of Higher Olefins Using Molecular Oxygen," Applied Catalysis A: General 221 (2001) 73-91.
C. Qui et al., "Epoxidation of Propylene Over Gold Catalysts Supported on Non-Porous Silica," Applied Catalysis A: General 218 (2001) 81-89.
R. Meiers et al., "Synthesis of Propylene Oxide from Propylene, Oxygen, and Hydrogen Catalyzed by Palladium- Platinum-Containing Titanium Silicalite," Journal of Catalysis 176, 376-386 (1998) Article No. CA 982036.
W. Laufer et al., "Propylene Epoxidation with Hydrogen Peroxide Over Palladium Containing Titanium Silicalite," Journal of Molecular Catalysis A: Chemical 141 (1999) 215-221.
G. Li et al., "Effect of Sodium Ions on Propylene Epoxidation Catalyzed by Titanium Silicalite," Applied Catalysis A: General 218 (2001) 31-38.
English Abstract corresponding to BE 1011375 A6, 1997.
English Abstract corresponding to DE 19600709, 1997.
A. Van der Pol et al., "Oxidation of Linear Alcohols with Hydrogen Peroxide Over Titanium Silicate 1," Schuit Institute of Catalysis, Eindhoven Univ. of Technology, Appl. Catal. A., 106 (1) 97-113 (1993).
H. Gao et al., "Preparation of TS-1 Zeolite Suitable for Catalyzing the Epoxidation of Propylene," Shanghai Research Institute of Petrochemical Technology, Shanghai, Peoples Republic of China, Shiyou Xuebao, Shiyou Jiagong (2000) 16 (3), p. 39-84.
C. Dartt et al., "Synthesis and Physiochemical Properties of Zeolites Containing Framework Titanium," California Institute of Technology, Pasadena, CA, Microporous Matter, 2 (5), p. 425-437 (1994).
English Abstract of Belgian Patent No. 1,001,038, 1989.
English Abstract of JP 4-352771, 1992.

* cited by examiner

*Primary Examiner*—Bernard Dentz
(74) *Attorney, Agent, or Firm*—Kevin M. Carroll; Brooks Kushman P.C.

(57) ABSTRACT

Large crystals of titanium silicalite or intergrowths of intergrown smaller crystals, having a mean particle size greater than 2 μm, have been found catalytically effective at commercially reasonable rates for the epoxidation of olefins in the presence of hydrogen peroxide. Crystals synthesized with a silica source having a low sodium content exhibit high levels of production and selectivity. The crystals have a low attrition rate and are easily filterable from a product stream.

19 Claims, 2 Drawing Sheets

PROCESS FOR DIRECT OXIDATION OF PROPYLENE TO PROPYLENE OXIDE AND LARGE PARTICLE SIZE TITANIUM SILICALITE CATALYSTS FOR USE THEREIN

CROSS-REFERENCE TO RELATED APPLICATIONS

This application is a division of U.S. application Ser. No. 10/251,405; filed Sep. 20, 2002 now U.S. Pat. No. 6,960,671.

BACKGROUND OF THE INVENTION

1. Field of the Invention

The present invention pertains to the synthesis of propylene oxide from hydrogen peroxide in the presence of a titanium silicalite catalyst, or from hydrogen/oxygen mixtures in the presence of a commercially viable noble metal-treated titanium silicalite catalyst.

2. Background Art

Propylene oxide is an important alkylene oxide of commerce. Large amounts of propylene oxide are used, inter alia, for the preparation of nonionic polyether surfactants and of polyether polyols for manufacture of polyesters and other polymers, but in particular for polyols for manufacture of polyurethanes, the latter including both homopolymeric polyoxypropylene polyols and copolymeric polyols prepared using other alkylene oxides, particularly ethylene oxide, in addition to propylene oxide. Propylene oxide also has numerous other uses in organic synthesis.

Older methods of propylene oxide production employed the "epichlorohydrin" process, a process which employs toxic chlorine, and generates numerous chlorine-containing byproducts which present environmental concerns but is still in use today. Several "coproduct" processes have been disclosed and/or implemented. In one major commercial process, indirect oxidation of propylene by ethylbenzene oxidation products to form propylene oxide yields styrene as a major coproduct. In both this as well as other coproduct processes, the economic value of the coproduct has a great effect on the overall process economics. The value of the coproducts may at times by undesirably low. Thus, it is desirable to employ a process which does not rely on coproduct economics to produce propylene oxide.

A "direct" method of propylene oxide production has long been sought. In such "direct" methods, propylene oxide is produced by oxidation of propylene with oxygen or with a "simple" oxidizing precursor such as hydrogen peroxide, without the use of significant amounts of co-reactants and concomitant generation of co-products from these co-reactants. Even though a great deal of research has been expended in these efforts, "direct" production of propylene oxide has not heretofore become a commercial reality.

In U.S. Pat. No. 5,401,486, it is disclosed that propylene oxide may be produced by the "direct" oxidation of propylene by hydrogen peroxide in the presence of a titanium silicalite catalyst, citing EP A-100,118. However, the latter indicates that the principle products of olefin oxidation are ethers, with olefin oxides prepared only in minor amounts. The titanium silicalite useful in such processes, despite the relatively low yield of olefin oxides, has been generally acknowledged by the art to be limited to exceptionally small titanium silicalite crystals substantially free of the anatase form of titanium silicalite. These crystals are about 0.2 μm or less in size. Since the catalysts are heterogenous catalysts, use of larger particle size catalysts, with their decreased surface area, should result in a considerable decrease of activity and product yield in the oxidation of alkenes. For example, the rate of oxidation of linear alkanols employing titanium silicalites has been shown to be reduced as crystal size of the titanium silicalite is increased. See, e.g., "Oxidation of Linear Alcohols with Hydrogen Peroxide Over Titanium Silicalite 1," A. Van der Pol et al., Schuit Institute of Catalysis, Eindhoven University of Technology, APPL. CATAL. A., 106(1) 97-113 (1993), which indicates that a particle size less than 0.2 microns is necessary to obtain maximum catalyst activity. See also U.S. Pat. No. 6,106,803, which indicates that high catalytic activity can only be obtained with small primary crystals of titanium silicalite. The 6,106,803 patentees teach preparing small primary crystals and using these crystals to form granulates of larger size by spray-drying. These and other publications have discouraged investigation of the use of large titanium silicalite crystals.

Other references which relate more directly to olefin epoxidation indicate that selectivity and hydrogen peroxide conversion efficiency are decreased by the presence of anatase in the titanium silicalite catalyst. See, e.g., "Preparation of TS-1 Zeolite Suitable for Catalyzing the Epoxidation of Propylene," H. Gao et al., Shanghai Research Institute of Petrochemical Technology, Shanghai, Peoples Republic of China, Shiyou Xuebao, Shiyou Jiagong (2000) 16 (3), p. 79-84; and "Synthesis and Physicochemical Properties of Zeolites Containing Framework Titanium," C. Dartt et al., California Institute of Technology, Pasadena, Calif., MICROPOROUS MATTER, 2 (5) p. 425-437 (1994).

However, use of small titanium crystals, e.g. those having mean sizes of about 0.2 μm or less is highly problematic in commercial epoxidation of alkenes. In fixed bed processes, the small particle size creates an enormous pressure drop which renders the process unworkable, while in slurry processes, separation of the catalyst from the liquid reactor contents is extremely difficult. Moreover, due to the attrition of particulate catalysts in commercially useful reactors, the particle size decreases over time, eventually plugging filters designed to recover and recirculate catalyst back to the reactor. As a result, although the catalyst activity of small particle size catalysts is reasonably high, a commercial process employing such catalysts is not practical.

To improve the longevity of the olefin epoxidation process, small titanium silicalite crystals have been conglomerated into formed particles of larger size through the use of binders, as taught, for example, by U.S. Pat. Nos. 5,500,199 and 6,106,803. However, such conglomerated catalysts suffer from several defects. The binder, though porous, will necessarily obscure portions of the zeolite structure, thus effectively removing such portions as catalytic sites in the reaction. Unless the binder has high adhesive and cohesive strength, the formed particles will again be subject to attrition as the conglomerates break apart. Increasing binder content can minimize attrition, although the likelihood of obscuring catalytic sites is then higher. Moreover, the catalyst is essentially "diluted" by the binder on a weight/weight basis, thus requiring greater amounts of catalyst for the same epoxide production rate.

It would be desirable to directly epoxidize propylene in the presence of large titanium silicalite crystals which exhibit high activity, low attrition rates, and freedom from use of binders, and which do not cause rapid plugging of catalyst filter elements.

SUMMARY OF THE INVENTION

It has now been surprisingly discovered that large sized crystals of titanium silicalite and crystal intergrowths thereof may be used in alkene epoxidation at commercially useful epoxidation rates despite the prejudice of the art against the use of such large sized particles. It has been further surprisingly discovered that the silica source material can markedly affect catalytic activity. Alkene epoxidation processes employing large crystals and intergrowths generate fines much less rapidly, and thus alkene epoxidations employing such catalysts can run for extended periods without shutdown, and with considerably less addition of new catalyst to the process.

DETAILED DESCRIPTION OF THE PREFERRED EMBODIMENT(S)

The present invention pertains to alkene epoxidation in the presence of titanium silicalite catalyst particles having an average particle size of greater than 2 microns. The size of the particles can be measured by scaling from scanning electron micrographs or via methods which are based on laser dispersion methods. Epoxidation in the subject invention process may be by hydrogen peroxide or by a mixture of hydrogen and oxygen when a suitable noble metal-treated catalyst is used. As used herein, the term "epoxidation" refers to processes using either set of epoxidizing reactants set forth above unless indicated otherwise. The use of hydrogen and oxygen may be termed an "in situ" process, since hydrogen peroxide is generated in situ. In the latter process, the preferred catalyst is a palladium-treated titanium silicalite, although other palladium catalysts and other metal catalysts may be used in conjunction with titanium silicalite epoxidation catalysts. Examples of such metal catalysts include but are not limited to Ni, Pd, Pt, Cu, Ag, and Au. Noble metal catalysts are presently preferred.

The alkene which is epoxidized is a $C_3$ or higher alkene, preferably propylene, although the process is also useful with other alkenes such as $C_{4-20}$ alkenes, more preferably $C_{4-8}$ alkenes, and yet more preferably $C_4$ alkenes such as 1-butene and 2-butene. Cyclic alkenes such as cyclohexene and cyclopentene are also useful, as are dienes and polyenes, for example 1,3-butadiene. The epoxidation preferably takes place continuously, for example in continuous stirred tank reactors (CSTR), tubular reactors, fixed bed and fluidized reactors, and the like. In such processes, alkene and epoxidizing agent are fed to the reactor and contacted with the solid titanium silicalite catalyst. The temperature is adjusted to achieve a reasonable reaction rate without generation of byproduct types and amounts which would render sustained operation problematic. Reaction temperatures of 25° C. to 100° C. are preferred, more preferably 30° C. to 80° C., and most preferably 40° C. to 70° C. Selection of the reaction temperature, reactor pressure, byproduct separation, and product purification are easily made by one skilled in the art.

Most preferably, the process is an in situ process employing hydrogen, oxygen, and a catalyst suitable for forming hydrogen peroxide in situ. Since hydrogen and oxygen are "permanent gases," unreacted portions may easily be separated from the reactor and recycled. Palladium is the preferred noble metal catalyst, but other noble metals which catalyze generation of hydrogen peroxide may be used as well, for example Pt, Au, and Ag. The noble metal may be supported on silica, thermoplastic beads, or any other convenient support. However, such supports occupy reactor volume but do not catalyze olefin epoxidation. It has been found that the noble metal may be deposited onto titanium silicalite, and the catalyst then performs the double function of both hydrogen peroxide generation and olefin epoxidation. Surprisingly, olefin epoxidation efficiency is maintained. Mixtures of untreated titanium silicalite and metal-treated titanium silicalite may also be advantageously used.

Figure 1:
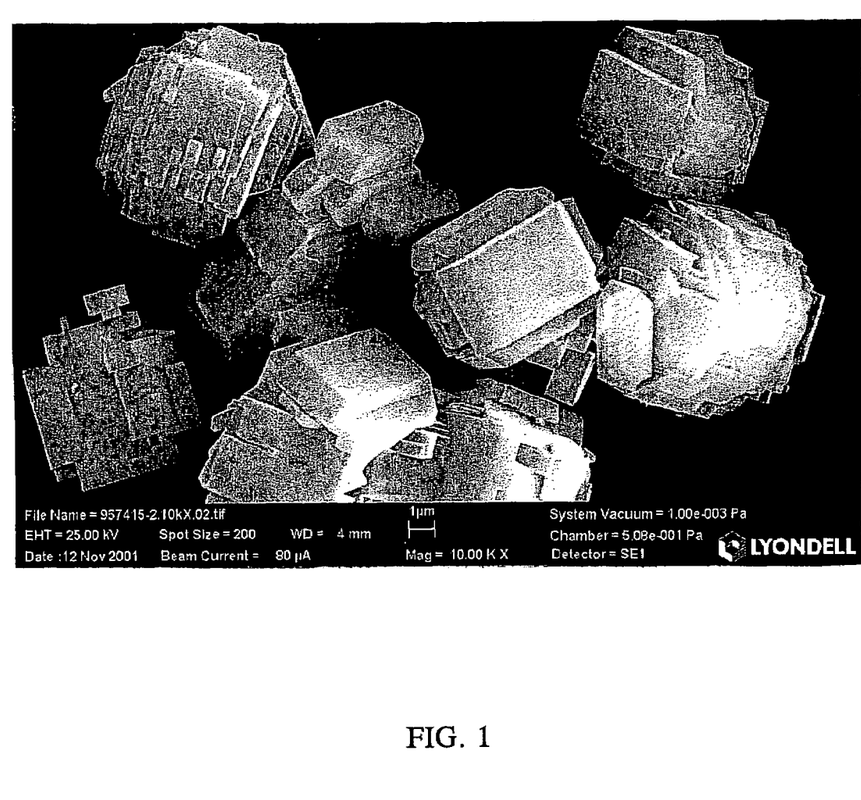
FIG. 1 is a scanning election micrograph of titanium silicalite intergrowths prepared according to one aspect of the invention.

The titanium silicalite catalysts useful in the present invention are titanium silicalite single crystals and intergrowths having a mean particle size greater than 2 μm. The term "intergrowth" should be contrasted with the prior use of "conglomerate" wherein sufficient binder is added to form a shaped product, and wherein binder surrounds significant portions of titanium silicalite crystals. The "intergrowths" of the present invention contain no binder to adhere crystals together. Most preferably, the crystals of the intergrowths are bound together by growth processes which yield an intertwined matrix of crystals with substantial integrity. An example of such intergrown crystals is shown in FIG. 1.

Figure 2:
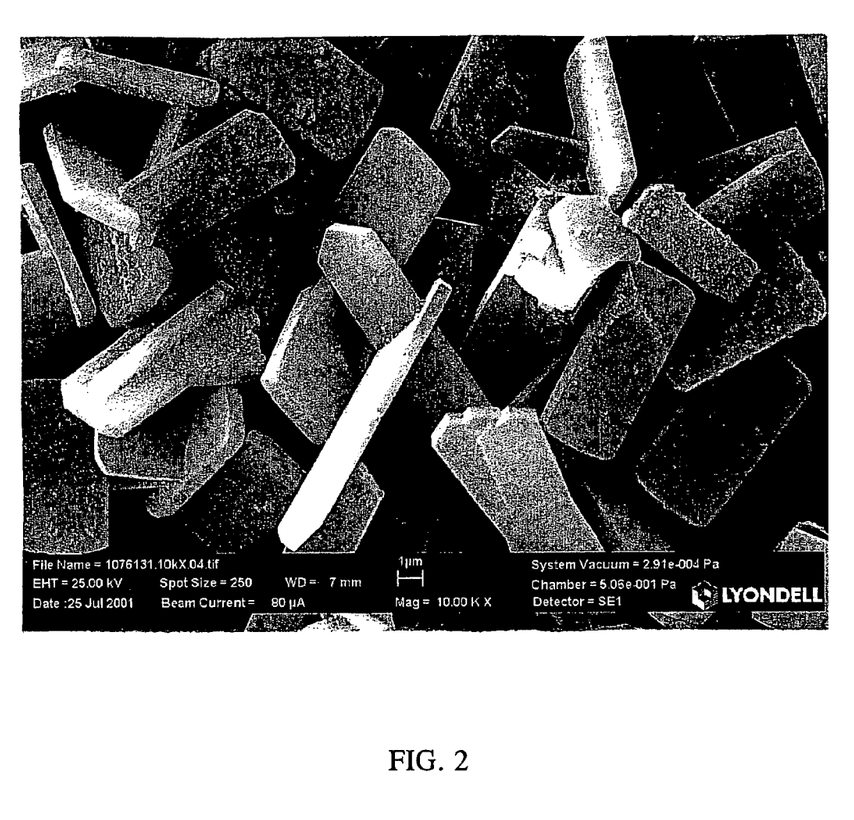
FIG. 2 is a scanning electron micrograph of non-intergrown large single crystal titanium silicalite prepared according to a further embodiment of the invention.

Single titanium silicalite crystals are generally flat rhombohedrons in shape. The minimum mean diameter (geometric) of single crystals across their major surfaces is 2 μm, but is preferably higher, i.e. 3-15 μm, more preferably 4-12 μm. At these large sizes, it is highly surprising that useful epoxidation rates can be maintained. Large single crystals are generally flat rhombohedrons having an aspect ratio (length/thickness) of about 1 to 10, more preferably 1 to 6, and most preferably about 1 to 5. Small aspect ratios, i.e. 1-2, are most preferred. The thickness of the crystals is relatively small, i.e., in the range of 0.3 to 5 μm, more preferably 0.4 to 3 μm, and most preferably 0.5 to 2 μm. An example of such crystals is shown in FIG. 2.

Use of intergrown titanium silicalite crystals for olefin epoxidation has not been disclosed. Intergrown crystals are comprised substantially of titanium silicalite, with "primary" rhombohedral crystals of relatively small size, i.e., preferably less than 5.0 μm in size across their major faces, and preferably less than 4 microns. The intergrowths are grown by processes wherein a considerable amount of intergrowth, "twinning," etc., takes place, such that the intergrowths have mean particle size (geometric mean in 3 dimensions) in excess of 2 μm, more preferably in the range of 2-30 μm, and most preferably in the range of 4-20 μm. Reference may be had to FIG. 1, where the mean particle size is about 4-5 μm. Surprisingly, it has been found that such intergrowths have even higher epoxidation performance than single crystals of the same mean size.

Large titanium silicalite single crystals may be made by processes known in the art, for example those disclosed by U.S. Pat. No. 5,401,486; EP 119 130; EP 543,247; and STUDIES IN SURFACE SCIENCE, V. 84, p. 203-210. Small crystal titanium silicalite (i.e. 0.2 μm) synthesis is described in U.S. Pat. No. 4,410,501. Most preferably a synthetic method as disclosed herein is used. In the preparation of large single crystal titanium silicalites, a range of particle sizes are generally produced.

For preparation of intergrown catalyst particles, any method which results in useful intergrowths having a particle (intergrowth) size greater than 2 μm may be used. It should be noted that such methods of intergrowth preparation must not involve preparation of small crystals followed by calcination with a binder as is used to form "shaped" or "formed" conglomerated catalyst particles. Rather, the crystal growth itself forms the intergrowth. Several examples of markedly different intergrown "crystallites" are presented herein. These methods are exemplary and not limiting.

In one method of titanium silicalite single crystal growth, a hydrolyzable precursor of titanium and a silica source, or hydrolyzable precursor(s) containing both silicon and titanium, are hydrolyzed in water, preferably in the presence of ammonia, hydrogen peroxide and a tetraalkylammonium compound such as a tetraalkylammonium halide. The first part of the preparation is conducted at 1 atm and mild temperatures, between 5° C. and 85° C., where "gel" is made. The second part of the preparation, a hydrothermal crystallization, is generally conducted in a sealed autoclave at elevated temperature, i.e. 150° C. to 200° C., under autogenous pressure. At the end of the growth period, for example 100 to 200 hours, the pressure is then released.

For the preparation of titanium silicalite intergrowths, crystal growth preferably occurs in a growth medium containing hydrolyzable titanium, hydrolyzable silica, and trtrapropylammonium hydroxide. The crystallization is preferably conducted at 130° C. to 200° C., more preferably at about 150° C. to 180° C. for an extended period, preferably for 1 to 8 days. The crystals are somewhat round (polyhedric) in appearance, and clearly exhibit numerous crystals and crystal faces. Scanning electron micrographs of a typical intergrowth is shown in FIG. 1. Preferred titanium and silica sources include alkyl- and alkoxy-functional siloxane/titanate copolymers. Such copolymers are commercially available. By the term "hydrolyzable titanium/silicon" copolymer is meant a composition containing both silicon and titanium, with hydrolyzable functionality such that a titanium silicalite may be obtained by hydrolysis. Titanium and silicon-linked hydrolyzable groups include, but are not limited to, alkoxy, hydrido, hydroxyl, halo, and like groups. With respect to titanium, alkyl and aryl groups may be present as well.

It has further been discovered that the use of raw material sources which are low in alkali metals and alkaline earth metals provide large crystal titanium silicalite products with unexpectedly enhanced activity. In particular, use of silica sources having less than 100 ppm sodium is highly desirable. Silica with even less sodium, for example about 50 ppm or less, and with low aluminum and iron content is also recommended. Sources of such highly pure silica include fumed silica which is commercially available.

The titanium silicalite catalysts of the present invention are preferably used in the previously described in situ process wherein hydrogen and oxygen rather than hydrogen peroxide are fed to the reactor as the source of oxygen for epoxidation. Under these conditions, the titanium silicalite is altered to contain a noble metal, preferably palladium, which may be applied to the titanium silicalite by conventional deposition processes. Any soluble palladium compound may be used in such deposition processes, or other methods of applying Pd may be used. Tetraamine palladium dichloride and tetraamine palladium dinitrate have both been used to successfully prepare palladium-treated titanium silicalite catalysts. Preferably, tetraamine palladium dinitrate without an excess of ammonia is employed. The titanium silicalite may be treated, for example, with a solution of soluble palladium at 80° C. for 24 hours for the nitrate and 20° C. for 1 hour for the chloride, followed by filtration and resuspension in deionized water. The product is then filtered and resuspended in deionized water twice more. The palladium-treated product may be isolated, dried in vacuum at 50° C. overnight, and calcined by heating in flowing 4 volume percent oxygen in nitrogen to 110° C. (10° C./min), holding for 1 hour, and heating at 2° C./min to 150° C. followed by a 4 hour hold. The weight percentage of palladium may range from 0.01 weight percent to about 2 weight percent or higher, but is preferably 0.1 to about 0.8 weight percent, more preferably 0.2 to 0.5 weight percent. Higher loadings of palladium can be accomplished by exposing a palladium-containing catalyst to further ion exchange from palladium solution followed by calcining, as described above. Further methods of depositing palladium and other catalytic metals may be found in the art of vehicular exhaust catalytic converters and other references dealing with noble metal deposition. The methods described above are not limiting.

Prior art catalysts have no commercial usefulness, as it is virtually impossible to maintain continuous reactor operation with mean particle sizes of 0.2 µm or less productivity due to clogging of filters. The present catalysts display an activity which is surprisingly high when viewed in conjunction with the increased particle size. Even though the present process has not been optimized, epoxidation rates similar and in some cases superior to those of the prior art small size titanium silicalite crystals have been achieved. Processes employing the larger catalysts of the subject invention can run for extended periods without shutdown. Thus, even for catalysts with lower production rates, the freedom from reactor down time makes these catalysts commercially viable.

Resistance to attrition is a necessary parameter for a commercial titanium silicalite epoxidation catalyst. Attrition may be measured by periodic sampling of solid catalyst from a reaction campaign, or may be assessed by an attrition test conducted in water or other suitable solvent, and described below. The latter test has been shown to accurately reflect attrition rate during epoxidation.

In the attrition test, a model reactor has a 3⅛ inch diameter I.D. and has a 2 inch diameter Rushton turbine with 6 vanes, rotating at 650 RPM. The baffle cage has 4 strips, each 5/16 inch wide. 50 gm of large crystal TS-1 are charged with 500 ml of deionized water and agitated at 20° C. No chemistry is conducted during the test. The titanium silicalite, when present as single crystals, is originally in the form of plates, normally with flat or slightly convex ends and straight sides. For example, in an actual test, measurements made directly from electron microscope images showed mean dimensions of 10.2×7.63×1.87 microns, approximately in accordance with the values from an automated laser-based technique. Samples are subjected to electron microscopy and particle size distribution measurement by laser dispersion, although any method of determining particle size and dimensions may be used. The volume-based median diameter ($d_{vol,50\%}$) and the number-based median diameter ($d_{n,50\%}$) may be extracted from the size distribution data, and show a slow disintegration over time. The electron micrographs show a steady increase in the proportion of fumes, mainly chips from the corners and the edges of the titanium silicalite platelets.

The volume and number-based median particle sizes may be plotted as the logarithms of their values against time in days, assuming that the size attrition is a first order process. A linear least squares fit yields the following equations tracking size attrition for the example described above:

$$d_{vol,50\%} \text{ (microns)} = 10^{-0.0009t+0.9799} \text{ t=time in days}$$
Equivalent to −0.21%/day $$d_{n,50\%} \text{(microns)} = 10^{-0.0005t+0.8974} \text{ t=time in days}$$
Equivalent to −0.12%/day These relationships generate plots which are properly of negative slope and of correct relative magnitude in the range of the data but intersect at high values of time. The particle size data at 0 hours were excluded from these curve fits because the first 24 hours of the test cause disintegration of loosely associated crystallites, which interferes with the data. Using these equations, the particle sizes at 180 and 365 days are projected to be as follows: $d_{vol,50\%}$ of 6.58 and 4.48 microns and $d_{n,50\%}$ of 6.42 and 5.19 microns. It should be noted that conglomerates prepared by spray-drying 0.2 μm titanium silicalite -crystals with kaolin or alumina binders exhibited a substantially higher attrition rate, expressed as the rate of decline in the median particle diameter based on volume, averaging 18.6%/day, far too high to be useful. The catalyst particles should have an attrition rate no higher than 2% (loss) per day, preferably less than 1% per day, and more preferably 0.5% or less per day.

The chemical efficiency of the various catalysts herein is assessed initially by a screening test in batch mode. The "screening test" is performed in a high pressure stainless steel autoclave, using hydrogen peroxide as the epoxidizing agent. The autoclave is charged with 40 g of 84 wt. % methanol, 4.8% hydrogen peroxide, balance water, and 0.15 g titanium silicalite-containing catalyst, the catalyst preferably being substantially all titanium silicaite. The reactor is sealed and heated to 50° C. and 19 g propylene injected. Agitation is provided by means of a stir bar, revolving at 600 RPM (10 $s^{-1}$). After 0.5 h, the reactor is shock chilled to stop the reaction, and residual propylene degassed into a gas bag. The propylene is weighed and analyzed, as is the aqueous phase remaining in the reactor. The hydrogen peroxide conversion efficiency, propylene oxide produced ("PO") and propylene oxide equivalents produced ("POE") are reported. By propylene oxide equivalents is meant propylene oxide and derivatives, i.e., propylene glycol, acetol, 1-methoxy-2-propanol, 2-methoxy-1-propanol, dipropylene glycol, tripropylene glycol, methoxydipropylene glycol, and methoxytripropylene glycol, among others. The selectivities are reported in percent as (mol PO/mol POE)×100%, measuring the relative extent of PO ring opening, and (mol POE/mol propylene consumed)×100%, measuring the selectivity of propylene conversion to POE. Another important measurement of selectivity is (mol POE/mol hydrogen peroxide consumed)×100% which measures the selectivity of hydrogen peroxide epoxidation of propylene to POE. In these experiments, the control catalyst for purposes of comparison is a titanium silicalite having a particle size of 0.2 μm and a Ti content of 1.1 wt. %.

In a preferred commercial olefin epoxidation process, the titanium silicalite epoxidation catalyst is slurried in a reaction mixture liquid phase which may preferably comprise water, lower alcohols, alkylalcohol ethers, ketones, and the like. The catalyst is preferably present in as large an amount which can be effectively maintained as a slurry, i.e., without undue sedimentation to a static bed. The reactor is preferably a draft tube reactor, as disclosed in U.S. Pat. No. 5,972,661, however other reactor configurations are possible, including tubular reactors and slurry reactors. Alternatively, the reactor may constitute a fixed bed of catalyst particles.

The reactant feed streams comprise, in addition to olefin, hydrogen peroxide and make-up solvent in the case of non-in-situ reactors, and hydrogen, oxygen, and make-up solvent in the case of in-situ reactors. Other reaction moderators, accelerators, buffers, etc. may be added as necessary. For example, an alkali metal hydrogen carbonate feed stream may be added. Triammonium phosphate, diammonium phosphate, monoammonium phosphate and mixtures thereof may be added as a feed stream. When. hydrogen peroxide is employed in a non-in-situ process, feed streams of oxygen and/or hydrogen may be introduced. In in-situ processes, likewise, a peroxide feed stream may be additionally introduced.

The reactor is maintained at a suitable temperature, as described previously, and a product take-off stream, containing alkylene oxide product, alkylene oxide equivalents, solvent, catalyst and catalyst fines, etc., is continuously removed from the reactor. From this product stream, large size catalyst particles, i.e. those having a size of >1 μm, preferably greater than 2 μm, may be recycled to the reactor, having been separated by conventional separating techniques, while catalyst fines, particularly those having a particle size <0.5 μm, more preferably <0.2 μm, are discarded or used as raw material for additional catalyst synthesis. In some processes, the product stream will contain substantially no catalyst particles, or only catalyst "fines," the bulk of the catalyst particles remaining in the reactor.

Alkylene oxide product is separated by distillation from the remaining non-solid components of the product stream, and reactor dispersion medium/solvent is advantageously recycled, any loss being made up of "make-up" solvent.

In the case of in-situ reactions, it is preferable that the reaction take place at relatively high pressure, i.e., at 50 to. 1500 psig, preferably 100 to 500 psig, and most preferably 100-200 psig and that substantially pure hydrogen and oxygen feeds be introduced into the reactor. While introduction of nitrogen or other inert gas is not precluded, obtaining effective concentration of hydrogen and oxygen at a given reactor pressure is rendered more problematic.

The gas oxygen and hydrogen partial pressures are adjusted to preferably product a gas composition below the explosion limit. Oxygen partial pressure is preferably 3 to 50 psig (122 to 446 kPa), more preferably 5 to 30 psig (135 to 308 kPa), and most preferably 5 to 20 psig (135 to 239 kPa), while the hydrogen partial pressure is preferably 2 to 20 psig (115 to 239 kPa), more preferably 2 to 10 psig (115 to 170 kPa), and most preferably 3-8 psig (122 to 156 kPa). Hydrogen and oxygen not reacted are preferably burned as fuel, rather than being recompressed and reused. However, it is also possible to recycle these components.

EXAMPLE 1

Titanium Silicalite Large Crystal Synthesis, Method 1

To a 3-neck flask is charged 51.06 g distilled water which is then cooled with agitation to 5° C. by means of an ice/water bath. A nitrogen blanket is established with an $N_2$ feed rate of 150 $cm^3$/m. To the cooled water, 4.4955 g titanium (IV) isopropoxide (98%, Strem 93-2216) is added, with vigorous stirring, following which 9.102 g 30% hydrogen peroxide is added to the flask over 15 min with very vigorous stirring. The flask is stirred for an additional 10 minutes at 5° C. The color of the solution turns yellow upon addition of the hydrogen peroxide, then gold and finally orange. To 254.237 gm of aqueous ammonia is added 45.763 g deionized water to form a 25 wt. % aqueous ammonia solution. The flask is removed from the ice bath, and 250.88 g of the 25% aqueous ammonia is added with continuous stirring. The solution becomes pale green with some white precipitate. The contents are stirred for 10 minutes, then heated to 80° C. and stirred at this temperature for 3 hours. The heat source is removed, and stirring continued overnight with nitrogen purge at 125 $cm^3$/m. The flask is weighed, and the remainder of the 25% aqueous ammonia added. The contents are stirred at high speed for 80 minutes.

To the flask, a mixture of 16.432 g tetrapropylammonium bromide solution in 49.75 g distilled water is added rapidly with sustained agitation. To the contents, 23.3 g Aerosil® 380 silica (Degussa) is then added, and mixed well.

The entire contents of the flask are transferred to a clean, Teflon-lined, unstirred 1000 ml autoclave which is flushed with nitrogen for 3-5 minutes at 100-150 cm$^3$/min to displace oxygen from the head space. Any positive pressure is released, and the autoclave sealed. The autoclave is heated to 185° C. and stirred at autogenous pressure for approximately 8 days. The autoclave is slowly cooled to room temperature, and the solid product isolated as a wet filter cake on a normal 5 μm filter, redispersed in 300 ml of 80° C. distilled water, agitated vigorously, and again filtered. This distilled water wash is repeated twice more, following which the catalyst is dried at 60° C. under vacuum overnight. The material is calcined for 4 hours at 110° C. in a Ney oven, followed by calcining at 550° C. for 6 hours in air. Prior to use, the subject invention catalysts were slurried in water and optionally filtered on 0.45 μm, 0.8 μm, or 5.0 μm filters, retaining the filtercake (and thus the larger particles).

In the general procedure set forth heretofore, the weight percentage of Ti may be adjusted by increasing or decreasing the amount of titanium (IV) isopropoxide initially added to the flask. The practical limit of Ti incorporation into the zeolite framework is circa 2.0 weight percent, according to the literature. Use of higher levels of titanium are said to result in anatase formation, which is stated to reduce yield in epoxidation with small (0.2 μm) crystals. Large crystals have been prepared with titanium contents of from about 1.3 to about 4 weight percent. It should be noted that the Teflon liner of the autoclave should be scrupulously cleaned between catalyst preparation, or a new liner installed.

COMPARATIVE EXAMPLE C1

A titanium silicalite catalyst having a mean particle size of 0.2 μm is prepared by methods of the prior art employing tetraethylorthosilicate as the silica source. See, e.g., U.S. Pat. No. 4,410,501, Example 1.

EXAMPLES 2-7 AND COMPARATIVE EXAMPLE C2

Large size titanium silicalites were prepared by the general method discussed previously and compared to a prior art titanium silicalite catalyst C1 exhibiting typical epoxidation activity and containing 1.1 wt. % titanium, all of which is believed to be incorporated as titanium silicalite in a zeolitic structure. The various catalysts were tested in the screening test described previously. The results are presented in Tables 1 and 2 together with the analytical and other data believed to be relevant. Complete elemental analyses were not performed for all catalysts. Example 7 consisted of large crystals from which fines were removed by filtration and tested for activity as Comparative Example C2.

TABLE 1

Large Crystal TS-1 Syntheses and Epoxidation Catalysis

| Catalyst | C1 | 1 | 2 | 3 | 4 |
|---|---|---|---|---|---|
| Theo. Ti (wt %) | NA | 1.38 | 2.76 | 2.76 | 1.38 |
| Filter | None | 0.45 micron | 0.8 micron | 0.8 micron | 5 micron |
| Elem. an. (wt %) | | | | | |
| Al | <0.01 | 0.028 | NS | 0.0465 | 0.042 |
| C | 0.39 | <0.1 | 0.39 | 0.1 | |
| Cl | <0.01 | <0.001 | <0.001 | <0.001 | |
| Cu | <0.001 | 0.0055 | <0.001 | <0.001 | |

TABLE 1-continued

Large Crystal TS-1 Syntheses and Epoxidation Catalysis

| Catalyst | C1 | 1 | 2 | 3 | 4 |
|---|---|---|---|---|---|
| Fe | <0.001 | 0.013 | 0.015 | 0.014 | <0.001 |
| H | 0.11 | <0.1 | <0.1 | <0.1 | |
| N | <0.1 | <0.1 | <0.1 | <0.1 | |
| K | <0.001 | <0.001 | 0.001 | <0.001 | |
| Na | <0.01 | 0.018 | NA | 0.145 | 0.052 |
| Si | 45 | 46 | 44 | 44.3 | 46 |
| Ti | 1.1 | 1.21 | 2.68 | 2.64 | 1.24 |
| Mean Length, μm | 0.2 | 12 | 8.5 | 6.7 | 5.8 |
| Mean Width, μm | 0.2 | 5 | 3.9 | 2.4 | 1.7 |
| Mean Thickness, μm | 0.2 | 1.7 | 0.87 | 0.78 | 0.52 |
| N$_2$ sur. area (m$^2$/g) | NA | 287 | NA | 316 | 371 |
| Estimated Ti in TS-1 framework relative to Ti(%)[1] | 100 | 40 | 48 | 41 | 52 |
| Estimated Ti in TS-1 framework (wt %)[1] | 1.1 | 0.478 | 1.29 | 1.09 | 0.644 |
| H$_2$O$_2$ conv (%) | 43 | 17.1 | 38.3 | 33.7 | 24.6 |
| PO (mmole) | 18.50 | 8.647 | 15.35 | 14.79 | 10.45 |
| POE (mmole) | 19.43 | 9.116 | 18.21 | 16.78 | 12.03 |
| POE selectivity relative to H$_2$O$_2$ (%) | 75.62 | 85.87 | 76.78 | 79.19 | 79.54 |

[1]Infra red spectroscopy yields a peak whose area is a proportional response to the concentration Ti which is tetravalent and in the titanium silicalite zeolite lattice and another peak whose area is proportional to the concentration of silicon in the material. The ratio of these two peak areas is proportional to the concentration in wt % of Ti which is in the TS-1 framework. These two variables have been correlated using TS-1 samples of known Ti content which have been shown by diffuse reflectance ultra violet spectroscopy and Xray spectroscopy to contain all the Ti in a zeolite framework. This method allows the Ti in the TS-1 framework of other samples to be determined and the proportion of that relative to the total Ti may be computed from the elemental analysis.

TABLE 2

Large Crystal TS-1 Syntheses and Epoxidation Catalysis

| Catalyst | C1 | 5 | 6 | C2 | 7 |
|---|---|---|---|---|---|
| Theo. Ti (wt %) | NA | 1.38 | 1.38 | 4.04 | 4.04 |
| Filter | None | 5 micron | 5 micron | 5 micron | 5 micron |
| Elem. an. (wt %) | | | | | |
| Al | <0.01 | 0.053 | 0.068 | NA | NA |
| C | 0.39 | | | | |
| Cl | <0.01 | | | | |
| Cu | <0.001 | | | | |
| Fe | <0.001 | 0.012 | 0.014 | 0.011 | NA |
| H | 0.11 | | | | |
| N | <0.1 | | | | |
| K | <0.001 | | | | |
| Na | <0.01 | 0.054 | 0.065 | NA | NA |
| Si | 45 | 46 | 45 | 44 | NA |

TABLE 2-continued

Large Crystal TS-1 Syntheses and Epoxidation Catalysis

| Catalyst | C1 | 5 | 6 | C2 | 7 |
|---|---|---|---|---|---|
| Ti | 1.1 | 1.14 | 1.25 | <0.001 | NA |
| Mean Length, μm | 0.2 | 8.5 | 8.1 | 10.8 | NA |
| Mean Width, μm | 0.2 | 2.6 | 1.6 | 2.5 | NA |
| Mean Thickness, μm | 0.2 | 0.72 | 0.62 | 0.81 | NA |
| $N_2$ sur. area ($m^2$/g) | NA | 351 | NA | 305 | NA |
| Estimated Ti in TS-1 framework relative to Ti(%)[1] | 100 | 64 | 46 | 21 | NA |
| Estimated Ti in TS-1 framework (wt %)[1] | 1.1 | 0.729 | NA | 0.639 | NA |
| $H_2O_2$ conv (%) | 43 | 21.34 | 19.98 | 7.09 | 32.08 |
| PO (mmole) | 18.50 | 8.00 | 7.91 | 10.66 | 14.20 |
| POE (mmole) | 19.43 | 9.76 | 9.38 | 11.85 | 16.69 |
| POE selectivity relative to $H_2O_2$ (%) | 75.62 | 74.66 | 76.6 | NA | 85.10 |

Tables 1 and 2 indicate that the large size titanium silicalite catalysts have slightly lower activity than the very small prior art catalysts. However, the decrease in activity is nowhere near that expected in view of the much larger catalyst particle size. Examples 2 and 3, for instance, exhibit an average loss in hydrogen peroxide conversion of only about 16%, while selectivity to propylene oxide actually increased somewhat. It is also surprising that the large size titanium silicalite catalysts showed greater activity when fines are increasingly removed. For example, the large titanium silicalites collected on 0.8 and 5 μm filters showed greater activity than those collected on 0.45 μm filters. One would expect the catalysts containing more small particles to exhibit a higher $H_2O_2$ conversion rate. However, this is not the case. In Example 7 and Comparative Example C2, the activity of the retains (large crystals) are compared with the activity of the crystals which pass through a 5 μm filter. The former gave an $H_2O_2$ conversion of 32.08% as compared to 7.09% for the fines, the opposite of what one would expect. The catalyst of Example 6 was slurried in 98% sulfuric acid, washed, dried at 110° C., and calcined. Prior to this treatment, the catalyst had shown relatively low activity (7.1% $H_2O_2$ conversion). Washing with sulfuric acid is one way of increasing catalytic activity. The titanium silicalite crystals were prepared by the general method heretofore described, employing Ludox AS40 colloidal silica (DuPont).

EXAMPLES 8-10

A variety of titanium silicalite catalysts were prepared from a silica source having a low sodium content. Fumed silica (Aerosil® 380, Degussa) was employed as the silica source. In addition to low sodium content, lower iron and aluminum content is present as compared to the Ludox® AS40 colloidal silica employed in the examples of Tables 1 and 2. The sodium content of Aerosil® 380 is less than 50 ppm as compared to 1300 ppm of the colloidal silica. Trials of a variety of titanium silicalites prepared using a low sodium silica source are compared with a conventional small size titanium silicalite catalyst of the prior art, and subject invention large size titanium silicalite catalysts prepared from a "high" sodium silica source. The relevant physical and chemical properties and catalytic activity are presented in Table 3 below.

TABLE 3

Large Crystal TS-1 Synthesis and Epoxidation Catalysts

| Catalyst | C1 | 4 | 5 | 7 | 8 | 9 | 10 |
|---|---|---|---|---|---|---|---|
| $SiO_2$ source |  |  |  |  | Low Na | Low Na | Low Na |
| Theo. Ti (wt %) | NA | 1.38 | 1.38 | 4.04 | 4.04 | 3.03 | 2.02 |
| Filter | None | 5 μm | 5 μm | 5 μm | 5 μm | 5 μm | 5 μm |
| Elem. an. (wt %) |  |  |  |  |  |  |  |
| Al | <0.01 | 0.042 | 0.053 | NA | 0.0051 | 0.0077 | <0.002 |
| C |  | 0.39 |  |  |  |  |  |
| Cl |  | <0.01 |  |  |  |  |  |
| Cu |  | <0.001 |  |  |  |  |  |
| Fe | <0.001 | <0.001 | 0.012 | NA | 0.0035 | 0.0034 | 0.005 |
| H |  | 0.11 |  |  |  |  |  |
| N |  | <0.1 |  |  |  |  |  |
| K |  | <0.001 |  |  |  |  |  |
| Na | <0.01 | 0.052 | 0.054 | NA | <0.005 | <0.005 | 0.005 |
| Si | 45 | 46 | 46 | NA | 43 | 44 | 45 |
| Ti | 1.1 | 1.24 | 1.14 | NA | 3.89 | 2.65 | 1.95 |
| Mean Length, μm | 0.2 | 5.8 | 8.5 | NA | 9.13 | 8.06 | 8.32 |
| Mean Width, μm | 0.2 | 1.7 | 2.6 | NA | 5.27 | 3.93 | 2.65 |
| Mean Thickness, μm | 0.2 | 0.52 | 0.72 | NA | 1.53 | 0.811 | 0.794 |
| $N_2$ sur. area ($m^2$/g) | NA | 371 | 351 | NA | 305 | 305 | NA |
| Estimated Ti in TS-1 framework relative to Ti(%) | 100 | 52 | 64 | NA | 34 | 57 | 72 |

TABLE 3-continued

Large Crystal TS-1 Synthesis and Epoxidation Catalysts

| Catalyst | C1 | 4 | 5 | 7 | 8 | 9 | 10 |
|---|---|---|---|---|---|---|---|
| Estimated Ti in TS-1 framework (wt %) | 1.1 | 0.644 | 0.729 | NA | 1.32 | 1.514 | 1.396 |
| $H_2O_2$ conv (%) | 43 | 24.6 | 21.34 | 32.08 | 32.52 | 39.60 | 34.10 |
| PO (mmole) | 18.50 | 10.45 | 8.00 | 14.20 | 14.69 | 21.21 | 16.95 |
| POE (mmole) | 19.43 | 12.03 | 9.76 | 16.69 | 16.56 | 23.72 | 18.75 |
| POE selectivity relative to $H_2O_2$ (%) | 75.62 | 79.54 | 74.66 | 85.10 | 77.44 | 97.95 | 88.88 |

The results in Table 3 indicate that by selecting a low sodium silica source, both $H_2O_2$ conversion efficiency and selectivity are high as compared to otherwise similar catalysts prepared from higher sodium content silica. Results at an intermediate Ti level (Example 9) exhibit nearly the same $H_2O_2$ conversion efficiency as the small titanium silicalite catalysts of the prior art (>90% relative to 0.2 μm crystals), while the propylene oxide equivalents selectively relative to hydrogen peroxide is truly excellent (ca. 98%). The amount of Ti employed (ca. 4 wt. %) is higher than can be incorporated into a TS-1 structure, contrary to the teachings of the prior art which indicate that non-framework Ti is detrimental.

Titanium Silicalite Crystalline Intergrowth Syntheses, Method 2

For preparation of intergrowths, tetrapropylammonium hydroxide or mixtures of tetralkylammonium hydroxide and tetraalkylammonium halide are used. Silica and titanium sources may be the same as for single crystal growth, but preferably used in Method 2 are siloxane/titanate copolymers such as alkoxysilane/alkyltitanate copolymers. One such copolymer is Gelest PSI TI-019, a diethoxysilane and ethyltitanate copolymer containing 19.4 wt. % silicon and 2.2 wt. % Ti. In general, a tetralkylammonium salt and a base are required. Suitable bases include organic amines, ammonia, and tetralkylammonium hydroxide.

EXAMPLE 11

An intergrown crystalline titanium silicalite (TS-1) catalyst was prepared by mixing together 6.8 g of a diethoxysilane-ethyltitanate copolymer (PSITI-109, Gelest, Inc.) containing 19.4 wt % Si and 2.2 wt % Ti, with 10 g of 40 wt % aqueous tetrapropylammonium hydroxide (Alfa) and 25 g water. The mixture was stirred and heated to 80° C. to remove ethanol by distillation. The volume was reconstituted with additional water and the mixture was introduced into a shaker bomb (autoclave) heated at 150° C. for 7 days. The solid product, 2.2 g of a white powder, was analyzed and found to contain 37 wt % Si, 1.1 wt % Ti, 9.2 wt % C and 0.99 wt % N. The x-ray diffraction pattern was consistent with pure titanium silicalite (TS-1). Scanning electron microscopy of the product indicated that relatively large (ca. 6-7 micron) crystalline agglomerates were produced, consisting of highly intergrown crystals.

EXAMPLE 12

A crystalline titanium silicate ETS-10 (Englehard) containing 66.1 wt % $SiO_2$, 10.0 wt % $Na_2O$, and 4.8 wt % $K_2O$ was ion-exchanged three times with 1M $NH_4NO_3$ at 80° C. To 10 g 40% tetrapropylammonium hydroxide (Alfa) in 25 g water, was added 5.0 g of the ion-exchanged product from above. The mixture was introduced into a shaker bomb maintained at 180° C. for 5 days. The recovered product was pure titanium silicalite (TS-1) by x-ray diffraction, and analyzed for 39 wt % Si and 1.7 wt % Ti. SEM showed crystalline agglomerates, in the size of ca. 3 microns, with a high degree of intergrowth.

EXAMPLE 13

A mixture was prepared containing 7.14 g TEOS (tetraethyl orthosilicate), 7.07 g titanium-(triethanolaminato) isopropoxide (80% in isopropyl alcohol), 21 g water, 7.39 g 40 wt % tetrapropylammonium hydroxide (Alfa), and 0.43 g HZSM-5 (CBV-10002 from PQ, with Si/Al=255). The mixture was heated in a shaker bomb at 150° C. for 7 days. 2.38 g of a white solid was recovered, and shown to be pure titanium silicalite (TS-1) by XRD. After calcination in air at 550° C., the solid analyzed for 41 wt % Si and 1.2 wt % Ti. SEM indicated the presence of crystalline intergrowths, 5-10 microns in size.

EXAMPLE 14

A mixture of 3.97 g of an amorphous titanosilicate (containing 7.0 wt % Ti and 38 wt % Si), 10.0 g 40% tetrapropylammonium hydroxide, 23.9 g water, and 0.4 g HZSM-5 (CBV-10002 from PG, with Si/Al–255) was heated in a shaker bomb at 180° C. for 4 days. 3.97 g of a white solid was recovered and shown to be pure TS-1 by XRD. After calcination in air at 550° C., the product analyzed for 1.6 wt % Ti and 41 wt % Si. SEM indicated the presence of crystalline intergrowths, greater than 5 microns in size.

EXAMPLE 15

An intergrowth crystalline titanium silicalite (TS-1) catalyst was prepared by mixing together 6.99 g of a diethoxysilane-ethyltitanate copolymer (PSITI-019, Gelest, Inc.) containing 19.4 wt % Si and 2.2 wt % Ti, with 1.97 g tetrapropylammonium bromide, 0.31 g calcined TS-1 (1.45 wt % Ti), 1.02 g 40 wt % aqueous tetrapropylammonium hydroxide (from Alfa), and 28 g water. The mixture was heated in a shaker bomb at 150° C. for 7 days, and a solid product, 3.56 g, was recovered. The x-ray diffraction pattern was consistent with pure titanium silicalite. Scanning electron microscopy of the product indicated that relatively large (ca. 6-8 micron) crystalline agglomerates were produced, consisting of highly intergrown crystals.

EXAMPLE 16

An intergrown crystalline titanium silicalite (TS-1) catalyst was prepared by mixing together 5.99 g of a diethoxysilane-ethyltitanate copolymer (PSITI-019, Gelest, Inc. containing 19.4 wt % Si and 2.2 wt % Ti), which was preheated at 75° C. for 2 hours with 0.33 g of a calcined TS-1 containing 1.45 wt % Ti, 10.07 g 40 wt % aqueous tetrapropylammonium hydroxide (from Alfa), and 20 g water. The mixture was heated in a shaker bomb at 200° C. for 2 days, and a solid product, 3.1 g, was recovered. The x-ray diffraction pattern was consistent with pure titanium silicalite (TS-1). After calcination at 550° C., the product analyzed for 4.0 wt % Ti and 39 wt % Si. Scanning electron microscopy of the product indicated that relatively large crystalline agglomerates were produced, consisting of highly intergrown crystals.

EXAMPLE 17

An intergrown crystalline titanium silicalite (TS-1) catalyst was prepared by mixing together 10.03 g of a diethoxysilane-ethyltitanate copolymer (PS9150, United Chemical Technology, Inc., containing 44-47 wt % $SiO_2$ and $TiO_2$ with Si/Ti–12-13), which was preheated under flowing nitrogen at 80° C. for one hour with 0.33 g of a calcined TS-1 containing 1.45 wt % Ti, 10.04 g 40 wt % aqueous tetrapropylammonium hydroxide (from Alfa), and 20 g water. The mixture was heated at 550° C., the product analyzed for 3.5 wt % Ti and 29 wt % Si. Scanning electron microscopy of the product indicated that relatively large crystalline agglomerates were produced, consisting of highly intergrown crystals.

EXAMPLE 18

An intergrown crystalline titanium silicalite (TS-1) catalyst was prepared by mixing together 7.06 g of a diethoxysilane-ethyltitanate copolymer (PSITI-019, Gelest, Inc. containing 19.4 wt % Si and 2.2 wt % Ti), which was preheated at 75° C. for 2 hours with 0.35 g of a calcined TS-1 containing 1.45 wt % Ti, 10.52 g 40 wt % aqueous tetrapropylammonium hydroxide (from Alfa), and 20 g water. The mixture was heated in a shaker bomb at 180° C. for 3 days, and a solid product, 3.24 g, was recovered. The x-ray diffraction pattern was consistent with pure titanium silicalite (TS-1). After calcination at 550° C., the product analyzed for 1.3 wt % Ti and 41 wt % Si. Scanning electron microscopy of the product indicated that relatively large crystalline agglomerates were produced, consisting of highly intergrown crystals.

EXAMPLE 19

An intergrown crystalline titanium silicalite (TS-1) catalyst was prepared by mixing together 13.6 g of a diethoxysilane-ethyltitanate copolymer (PSITI-019, Gelest, Inc.) containing 19.4 wt % Si and 2.2 wt % Ti, with 2.7 g tetrapropylammonium bromide, 5 g 40 wt % aqueous tetrapropylammonium hydroxide (from Alfa) and 36 g water. The mixture was stirred and heated to 80° C. to remove ethanol by distillation. The volume was reconstituted with additional water and the mixture was introduced into a shaker bomb (autoclave) heated at 175° C. for 5 days. The solid product, 5.07 g of a white powder, was analyzed and found to contain 38 wt % Si, 2.2 wt % Ti, 9.0 wt % C and 0.92 wt % N. The x-ray diffraction pattern was consistent with pure titanium silicalite (TS-1). Scanning electron microscopy of the product indicated that relatively large crystalline agglomerates were produced, consisting of highly intergrown crystals.

EXAMPLE 20

An intergrown crystaline titanium silicalite (TS-1) catalyst was prepared by mixing together 19.98 g of a diethoxysilane-ethyltitanate copolymer (PSITI-019, Gelest, Inc.) containing 19.4 wt % Si and 2.2 wt % Ti, with 1.05 g HZSM-5 (from PQ, CBV-10002, Si/Al=255). The mixture was heated at 70° C. for 2 hours, then kept overnight at room temperature. 7.37 g of this mixture was then added to 10.0 g 40% tetrapropylammonium hydroxide (from Alfa) in 20.1 g water. The mixture was introduced into a shaker bomb (autoclave) and heated at 175° C. for 5 days. The solid product, 4.14 g of a white powder, exhibited the x-ray diffraction pattern of pure titanium silicalite (TS-1). After calcination at 550° C., the product analyzed for 1.3 wt % Ti and 44 wt % Si. Scanning electron microscopy of the product indicated that relatively large crystalline agglomerates were produced, consisting of highly intergrown crystals.

EXAMPLE 21

An intergrown crystalline titanium silicalite (TS-1) catalyst was prepared by mixing together 6.86 g of a diethoxysilane-ethyltitanate copolymer (PSITI-019, Gelest, Inc.) containing 19.4 wt % Si and 2.2 wt % Ti, with a solution of 2.0 g tetrapropylammonium bromide and 20 g concentrated ammonium hydroxide in 20 g water. The mixture was introduced into a shaker bomb (autoclave) and heated at 175° C. for 7 days. The solid product, 2.3 g of a white powder, exhibited the x-ray diffraction pattern of pure titanium silicalite (TS-1). After calcination at 550° C., the product analyzed for 4.1 wt % Ti and 42 wt % Si. Scanning electron microscopy of the product indicated that extremely large crystalline agglomerates (greater than 20 microns in size) were produced, consisting of highly intergrown crystals.

Catalysis:

Propylene Epoxidation with Pre-formed Hydrogen Peroxide

Intergrown titanium silicalite catalysts were evaluated for epoxidation activity by the standard screening test described earlier. The results are shown below:

| Catalyst | Ex. 13 | Ex. 14 | Ex. 15 | Ex. 16 | Ex. 17 | Ex. 18 | Ex. 19 | Ex. 20 |
|---|---|---|---|---|---|---|---|---|
| $H_2O_2$ Conversion (%) | 46.8 | 31.0 | 49.4 | 54.3 | 58.9 | 60.0 | 45.9 | 48.8 |
| PO (mmol) | 25.2 | 18.7 | 26.2 | 30.4 | 34.0 | 34.2 | 25.3 | 27.2 |
| POE (mmol) | 29.3 | 20.3 | 28.9 | 33.3 | 37.7 | 35.6 | 26.5 | 29.0 |

The results indicate even higher activity than that of many 0.2 μm single crystals of the prior art, which is highly surprising in view of the limited surface area of the intergrown crystals as compared to 0.2 μm single crystals.

General Method, Continuous in Situ Epoxidation

For continuous in situ olefin epoxidation, a Pd-treated catalyst is slurried at 100 g catalyst/liter in 75/25 (w/w) methanol/water. Reactant feeds consist of liquid propylene and a gas mixture comprising $O_2$, $N_2$, and $H_2$. A cylindrical stainless steel pressure reactor is used, with a 2 inch diameter Rushton turbine impeller providing agitation. The reactor has an essentially flat bottom surface, with about ¼ inch radius concave peripheral chamfers. The impeller is located above the upper active face of a filter in the form of a ring of sintered 316 stainless steel. The filtered fluid passes into a channel which is machined in the filter body and which passes around the entire ring.

The hydrogen feed is supplied through a port in the base of the vessel. The liquid propylene feed and previously mixed methanol and water solvent feed are combined externally to the reactor and fed through a dip tube to a point above the base of the vessel. Each gas feed is monitored via a gas mass flow meter, while liquid feeds are monitored via liquid mass flow meters. The exit gas and filtered exit liquid are analyzed every 2 hours by in-line GC.

The reactor liquid level is controlled by measuring the difference in pressure between the oxygen feed gas dip tube, which terminates close to the base of the vessel, and the head space of the reactor. The differential pressure cell has a range of 20 inches water gauge. Deviations in the level from the controller set point (normally 4.0 to 5.0 inches) result in corrective action via the flow rate control valve in the filtered liquid exit line.

The reactor is usually run at 500 psig and 45° C. or 60° C. There is no draught tube in the reactor and it is intermediate between lab and pilot plant scales. Several in situ runs employing Pd-treated titanium silicalite catalyst were made.

EXAMPLE 22

The results are presented in Table 5. In Tables 5 and 6, abbreviations such as SPPO, SOPO, etc., refer to selectivity (S) based on propylene feed (P), hydrogen feed (H) or oxygen feed (O) with respect to the particular product, i.e. propylene oxide (PO), propylene oxide equivalents (POE), ring opened products (RO:POE minus PO), propane, water, or carbon dioxide. Thus, SPPO is the selectivity (mol/mol) of propylene conversion to propylene oxide, while SOPO is the selectivity of oxygen conversion to propylene oxide.

TABLE 5

Continuous Reaction Using Pd on Large TS-1 Crystals (Example 22)

| Time Period Designation | 1<br>After Break-in<br>Maximum POE Best<br>Overall Performance | 2<br>Hydrogen Feed<br>Rate Reduced | 3<br>Overall Run,<br>After Break-in |
|---|---|---|---|
| Start time (hr) | 25.98 | 137.97 | 25.98 |
| End time (hr) | 76.00 | 165.95 | 165.95 |
| Duration (hr) | 50.02 | 27.98 | 139.97 |
| Feed ratios | | | |
| Propylene/hydrogen | 1.86 | 2.14 | 1.92 |
| Oxygen/hydrogen | 2.00 | 2.30 | 2.07 |
| Exit partial pressure (psi) | | | |
| Propylene | 7.42 | 12.00 | 9.59 |
| Oxygen | 18.63 | 19.45 | 18.90 |
| Hydrogen | 2.25 | 3.37 | 3.06 |
| Conversion (%) | | | |
| Propylene | 20.18 | 9.71 | 14.40 |
| Oxygen | 15.00 | 16.33 | 17.06 |
| Hydrogen | 76.12 | 62.81 | 68.84 |
| Rate | | | |
| PO productivity (gmPO/gcathr) | 0.017 | 0.020 | 0.019 |
| RO productivity (gmPO/gcathr) | 0.031 | 0.022 | 0.028 |
| POE productivity (gmPO/gcathr) | 0.047 | 0.042 | 0.045 |
| POE productivity (gmPO/liter slurry hr) | 4.7 | 4.2 | 4.5 |
| PO/POE (%) | 35.00 | 48.02 | 42.66 |
| Propylene Selectivity | | | |
| SPPO (%) | 30.34 | 39.78 | 35.75 |
| SPRO (%) | 56.93 | 43.10 | 48.68 |
| SPPOE (%) | 87.28 | 82.89 | 84.43 |
| SPPropane (%) | 11.76 | 16.56 | 14.83 |
| $SPCO_2$ (%) | 0.97 | 0.55 | 0.73 |
| Oxygen Selectivity | | | |
| SOPO (%) | 14.45 | 22.69 | 18.52 |
| SORO (%) | 28.99 | 24.73 | 25.05 |
| SOPOE (%) | 41.45 | 47.42 | 43.57 |
| $SOH_2O$ (%) | 56.66 | 51.17 | 54.84 |
| $SOCO_2$ (%) | 1.89 | 1.40 | 1.59 |
| Hydrogen Selectivity | | | |
| SHPOE (%) | 31.05 | 25.93 | 26.69 |
| SHPropane (%) | 3.18 | 6.27 | 4.91 |
| $SHH_2O$ (%) | 65.77 | 67.80 | 68.40 |

EXAMPLES 23-26

Additional continuous runs have been conducted employing further catalysts. The results are presented in Table 6 below. Example 26 employed a 1:1 mixture of two palladium-treated catalysts, whose base catalysts, prior to Pd-treating, were prepared in the same manner and with the same reactants and reactant ratios as the base catalyst of Example 24, i.e. Example 9 of the subject invention. The respective base catalyst particles had mean dimensions of 9.69×3.65×1.038 μm and 5.91×2.66×0.595 μm, respectively. Analysis revealed 3.08 and 3.18 weight percent titanium as compared to 2.65 weight percent titanium of the base catalysts of claim 26. Screening test results showed 35.8 and 40.69 $H_2O_2$ percent conversion, and 19.87 and 22.61 mmol POE. POE selectivity was 91.42 and 90.89, respectively. The Pd-treated catalysts of Example 26 were treated with $Pd(NH_3)_4 (NO_3)_2$ and calcined as previously disclosed. Pd weight percent was 0.49.

TABLE 6

| | Example | | | |
|---|---|---|---|---|
| | 23 | 24 | 25 | 26 |
| Large TS-1 Prep | Example 8 | Example 9 | — | See text |
| Mass cat (gm) | 16.14 | 15.2 | 40.07 | 37.22 |
| Vol Slurry (ml) | 400 | 400 | 400 | 400 |
| Cat conc (gm/100 ml) | 4.035 | 3.8 | 10.02 | 9.305 |
| Hours on Stream (hr) | 235 | 91.23 | 166 | 102 |
| Press (psig) | 500 | 500 | 500 | 500 |
| Temp (C.) | 60 | 60 | 60 | 60 |
| Agit (RPM) | 750 | 750 | 750 | 750 |
| Feed Composition (wt %) | 90 methanol 10 water | 75 methanol 25 water | 75 methanol 25 water | 75 methanol 25 water |
| Ammonium Bicarbonate Feed (ppm in liquid feed) | Zero | 71 | 150 (0-46.5 hr) 285 (46.5-166 hr) | 2000 (0-48 hr) 1000 (48-102 hr) |
| Peak POE (gmPO/gmcat hr) | 0.07 | 0.15 | 0.055 | 0.32 |
| At POE peak: | | | | |
| SPPOE (%) | 93 | 93 | 88 | 84 |
| SOPOE (%) | 10 | 58 | 46 | 60 |
| SHPOE (%) | 5 | 39 | 28 | 35 |
| Mean POE (gmPO/gmcat hr) | 0.03 | 0.107 | 0.045 | NA |
| Mean: | | | | |
| SPPOE (%) | 10 | 91 | 84 | NA |
| SOPOE (%) | 5 | 36 | 44 | NA |
| SHPOE (%) | 3 | 22 | 27 | NA |

The results indicate that significant in situ epoxidation has occurred. It should be noted that the results are based on a relatively small scale reactor, using considerable nitrogen in the oxygen feed. In a commercial reactor, both the reactor pressure as well as the partial pressure of oxygen are expected to be changed to higher values, i.e., using a pure oxygen feed.

EXAMPLE 27

In-situ Propylene Epoxidation with Hydrogen and Oxygen

To 1 g of intergrown catalyst of Example 11 dispersed in 87 g methanol was added 0.0181 g palladium tetraamine dibromide dissolved in 20 g water. This mixture was stirred at room temperature for 2 hours. The temperature was then raised to 45° C. and, at atmospheric pressure, flows of 20% $H_2$/80% propylene at 25 $cm^3$/min and 5% $O_2$/0.6% $CH_4$/94.4% $N_2$ at 88 $cm^3$/min were introduced into the stirred slurry. Exit gas flows were analyzed by on line gas chromatography. At 30 hours on stream, the exit gas contained greater than 1600 ppm propylene oxide.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the preparation of a titanium silicalite catalyst comprising an intergrowth of titanium silicalite crystals having a mean particle size greater than 2 μm, said process comprising reacting a hydrolyzable titanium/silcon copolymer in the presence of a tetraalkylammonium hydroxide.

2. The process of claim 1, wherein said tetraalkylammonium hydroxide comprises tetrapropylammonium hydroxide.

3. A process for the preparation of a titanium silicalite catalyst comprising an intergrowth of titanium silicalite crystals having a mean particle size greater than 2 μm, said process comprising reacting a hydrolyzable titanium/silcon copolymer in the presence of a tetraalkylammonium salt and a base.

4. The process of claim 3, wherein said tetraalkylammonium salt is a tetrapropylammonium salt.

5. The process of claim 3, wherein said salt is a halide.

6. The process of claim 3, wherein said base comprises one or more of an organic amine, ammonia, or tetraalkylammonium hydroxide.

7. The process of claim 3, wherein said hydrolyzable titanium/silicon copolymer comprises an alkyl silicate/titanate copolymer.

8. A process for the preparation of titanium silicalite olefin epoxidation catalysts of improved catalytic activity, said process comprising: a) preparing titanium silicalite crystals by crystal growth from a growth medium comprising a hydrolyzable titanium/silcon copolymer, an alkylammonium salt and a base to form a titanium silicalite product containing crystals or intergrowths thereof having a particle size greater than 2 µm; b) filtering the titanium silicalite product with a filter medium having a mean pore size greater than 0.5 µm; and c) recovering a filter cake of titanium silicalite crystals or intergrowths thereof relatively depleted of crystals or intergrowths having particle sizes less than 2 µm as compared with the amount of crystals or intergrowths with particle sizes less than 2 µm obtained in step a).

9. The process of claim 8, wherein said base is an organic amine, ammonia, or a tetraalkylammonium hydroxide.

10. The process of claim 8, wherein said alkylammonium salt is a tetrapropylammonium salt.

11. The process of claim 8, wherein said filter medium has a mean pore size of from 1 µm to 8 µm.

12. The process of claim 8, wherein said filter medium has a mean pore size of from 2 µm to 7 µm.

13. An olefin epoxidation catalyst suitable for epoxidation of olefins with an oxidant mixture comprising oxygen and hydrogen, prepared by a process comprising: treating a titanium silicalite catalyst produced by the process of claim 1 with a noble metal source to provide a titanium silicalite catalyst containing a noble metal such that hydrogen peroxide is generated in situ from hydrogen and oxygen.

14. The catalyst of claim 13, wherein at least one noble metal is selected from the group consisting of palladium, gold, and platinum.

15. The catalyst of claim 13, wherein said noble metal comprises palladium.

16. An olefin epoxidation catalyst suitable for epoxidation of olefins with an oxidant mixture comprising oxygen and hydrogen, prepared by a process comprising: treating a titanium silicalite catalyst catalyst produced by the process of claim 3 with a noble metal source to provide a titanium silicalite catalyst containing a noble metal such that hydrogen peroxide is generated in situ from hydrogen and oxygen.

17. The catalyst of claim 16, wherein at least one noble metal is selected from the group consisting of palladium, gold, and platinum.

18. The catalyst of claim 16, wherein said noble metal comprises palladium.

19. An olefin epoxidation catalyst suitable for epoxidation of olefins with an oxidant mixture comprising oxygen and hydrogen, prepared by a process comprising: treating a titanium silicalite catalyst prepared by the process of claim 8 with a noble metal source to provide a titanium silicalite catalyst containing a noble metal such that hydrogen peroxide is generated in situ from hydrogen and oxygen.

* * * * *